(12) United States Patent
Sinha

(10) Patent No.: US 8,193,337 B2
(45) Date of Patent: Jun. 5, 2012

(54) OXIDATION PROCESS

(75) Inventor: Nanda D. Sinha, Boxborough, MA (US)

(73) Assignee: Avecia Biotechnology, Inc., Milford, MA (US)

(*) Notice: Subject to any disclaimer, the term of this patent is extended or adjusted under 35 U.S.C. 154(b) by 376 days.

(21) Appl. No.: 12/452,582

(22) PCT Filed: Jul. 14, 2008

(86) PCT No.: PCT/GB2008/002391
§ 371 (c)(1),
(2), (4) Date: Jan. 8, 2010

(87) PCT Pub. No.: WO2009/007736
PCT Pub. Date: Jan. 15, 2009

(65) Prior Publication Data
US 2010/0137572 A1 Jun. 3, 2010

(51) Int. Cl.
*C07H 21/00* (2006.01)

(52) U.S. Cl. ............... 536/25.33; 536/25.3; 536/25.31; 536/25.34

(58) Field of Classification Search .................. None
See application file for complete search history.

(56) References Cited

FOREIGN PATENT DOCUMENTS
WO    WO 03/004512 A    1/2003

*Primary Examiner* — Patrick Lewis
(74) *Attorney, Agent, or Firm* — Timothy E. Tinkler

(57) ABSTRACT

A process for the preparation of an oligonucleotide having at least one phosphate internucleotide linkage I provided. The process comprises the steps of:
a) forming a nascent oligonucleotide comprising a phosphorus (III) internucleotide linkage; and
b) oxidation of the nascent oligonucleotide with aqueous iodine solution thereby to form a phosphorus (V) internucleotide linkage;
wherein the oxidation is carried out in the presence of a base, the conjugate acid of said base having a pKa higher than the pKa of the conjugate acid of pyridine. Preferably the base is N-methylimidazole.

15 Claims, No Drawings

OXIDATION PROCESS

The present invention concerns a process for the preparation of oligonucleotides.

Oligonucleotides are important diagnostic and therapeutic compounds and many oligonucleotides are candidates in clinical trials for the treatment of many different conditions. Modern methods of synthesis of oligonucleotides typically involve the assembly of the desired oligonucleotide by coupling appropriate synthons to a nascent oligonucleotide in a sequence of deprotection and coupling steps. Most commonly, the synthon is a nucleoside phosphoramidite, although other synthons, such as nucleoside H-phosphonates are also available. The synthon typically comprises a reactive group for coupling with the coupling site on the nascent oligonucleotide, and a protected coupling site for the addition of the next synthon in the sequence. The coupling normally forms an internucleotide phosphorus (III) linkage which is subsequently converted to a phosphorus (V) linkage, commonly by the introduction of either sulphur or oxygen. Sulphur is introduced by use of well known sulphurising reagents. Oxidation is most commonly achieved by the use of iodine solution. Because a small portion of coupling sites remain unreacted after each coupling step, these sites are capped to prevent the so-called failure sequence reacting in subsequent couplings. This makes separation of the failure sequence from the full length product easier. After the coupling steps have been completed, the coupling site protecting group is removed and a further coupling step can then be carried out. A protecting group strategy is chosen such that only the protecting group at the desired coupling site is removed, and hence this site is available to react with the oligonucleotide synthon. Other potentially reactive sites remain protected, and therefore do not interfere with the desired coupling reaction.

Whilst numerous potential protecting groups and strategies are available, by far the commonest strategy is to employ an acid labile protecting group for the coupling site, with other protecting groups being inert under acidic conditions. The most preferred acid labile protecting groups are members of the trityl family, and especially dimethoxytrityl groups. Other, non-trityl acid labile protecting groups, such as pixyl groups, have also been proposed.

It remains desirable to identify alternative processes for the synthesis of oligonucleotides, especially processes which can offer improved yield of full-length product.

According to the present invention, there is provided a process for the preparation of an oligonucleotide having at least one phosphate internucleotide linkage comprising the steps of:
a) forming a nascent oligonucleotide comprising a phosphorus (III) internucleotide linkage; and
b) oxidation of the nascent oligonucleotide with aqueous iodine solution thereby to form a phosphorus (V) internucleotide linkage;
wherein the oxidation is carried out in the presence of a base, the conjugate acid of said base having a pKa higher than the pKa of the conjugate acid of pyridine.

In a related aspect, the present invention provides a process for the preparation of an oligonucleotide comprising at least one phosphate internucleotide linkage, the process comprising oxidising a phosphorus (III) internucleotide linkage with aqueous iodine solution in the presence of a base, the conjugate acid of said base having a pKa higher than the pKa of the conjugate acid of pyridine.

The pKa of the conjugate acid of pyridine is 5.25, and hence the conjugate acids of the bases employed in the process according to the present invention have a pKa of greater than 5.25. In some embodiments, the pKa of the conjugate acid of the base employed is 5.4 or greater, such as 5.7 or greater; commonly 6 or greater, such as 6.3 or greater; and preferably 6.5 or greater, such as 6.7 or greater. In many embodiments, the pKa of the conjugate acid of the base employed is less than 12, commonly 10 or lower, preferably 9 or lower and most preferably 8 or lower, such as 7.5 or lower. In certain especially preferred embodiments, the pKa of the conjugate acid of the base employed is from 6.5 to 7.5. Mixtures of two or more bases may be employed if desired. It will be recognised that the base employed is selected such that it does not adversely effect base-sensitive groups which may be present elsewhere in the oligonucleotide, such as base-labile protecting groups, under the conditions employed for the oxidation.

Organic bases which can be employed include aliphatic amines and aryl amines, particularly primary, secondary and tertiary amines, for example N,N-di$C_{1-4}$alkylanilines such as N,N-dimethylaniline and especially primary, secondary or tertiary $C_{1-4}$ alkyl amines. Preferred organic bases are heterocyclic compounds comprising 5, 6 or 7 cyclic atoms and one or, most preferably, two nitrogen atoms in the heterocyclic ring. It is especially preferred that the organic base employed is an aprotic base. Examples of preferred bases include imidazoles, such as imidazole and N—$C_{1-4}$ alkylimidazoles; substituted pyridines, such as di- and tri-$C_{1-4}$ alkyl pyridines, for example 2,3-dimethylpyridine, 2,4-dimethylpyridine, 3,5-dimethylpyridine and 2,4,6-trimethylpyridine.

Organic bases can be employed as a buffer solution.

Inorganic bases, such as alkali metal or ammonium phosphate salts can be employed. When inorganic salts are employed, they can be employed in the form of an aqueous buffer solution.

When buffer solutions are employed, they are selected to be more basic than the equivalent pyridine solution.

In certain embodiments, oxidation according to the present invention is achieved by employing an aqueous iodine solution comprising the base as an oxidant solution. Such iodine solutions typically comprise 20-100 mMol iodine in solution in a mixture of water miscible organic solvent and water, typically comprising up to 20% v/v water, preferably about 10% v/v water. The base the conjugate acid of which has a pKa greater than that of pyridine may, in some embodiments, be employed as the water-miscible organic solvent. In many embodiments, the base is employed in addition to the water-miscible organic solvent. A base which is solid at room temperature (20-25° C.) may be employed, dissolved in water or the water-miscible organic solvent and water mixture. Preferably the base is an organic base which is a liquid at room temperature and is employed as a mixture with the water-miscible solvent and water. Commonly, up to about 25% v/v of organic base is present, and preferably about 10% v/v. In certain preferred embodiments, the water miscible organic solvent is pyridine.

In other embodiments, especially where the oligonucleotide is being synthesised using solid phase chemistry, conventional iodine solutions can be employed, with contact between the iodine and the oligonucleotide comprising a P(III) internucleotide linkage in the presence of base the conjugate acid of which has a pKa greater than that of pyridine being achieved employing a step immediately preceding the oxidation, wherein the oligonucleotide comprising the P(III) internucleotide linkage is washed with a solution of said base. Such washing solutions commonly comprise up to 50% v/v base, and preferably from 10-30% v/v base, in one or more organic solvents. Preferably water miscible solvents or solvent mixtures, such as pyridine and acetonitrile, are employed. When such a washing step is employed, the solution of stronger base is preferably Cap A solution (20% v/v N-methylimidazole, 30% v/v pyridine in acetonitrile). The use of Cap A solution is particularly advantageous for automated synthesis because this reagent is typically already part of the standard reagent inventory for oligonucleotide synthesis, so no additional reagents and supply lines are needed.

Oligonucleotide synthons which can be employed in the process according to the present invention include nucleoside or oligonucleotide phosphoramidites, nucleoside or oligonucleotide H-phosphonates, especially 3'- or 5'-terminal ribo or deoxyribonucleoside H-phosphonate monoesters, and nucleoside or oligonucleotide phosphoramidates.

The process according to the present invention advantageously employs nucleoside phosphoramidites. Preferred protected nucleoside phosphoramidites are deoxyribonucleoside-3'-phosphoramidites or ribonucleoside-3'-phosphoramidites. It will be recognised that the invention is equally applicable to the use of 5'-phosphoramidites.

Examples of preferred protected nucleoside phosphoramidites are compounds of formula (1):

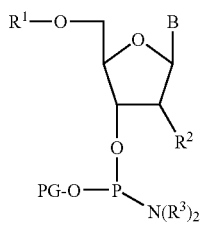

wherein $R^1$ is a protecting group, commonly an acid-labile protecting group, and preferably a trityl, monomethoxytrityl or dimethoxytrityl group, B is a nucleoside base, $R^2$ represents —H, —F, —OR$^4$, —NR$^5$R$^6$, —SR$^7$, or a substituted or unsubstituted aliphatic group, such as methyl or allyl. PG is a phosphorus protecting group, commonly a cleavable phosphorus protecting group employed in oligonucleotide synthesis, and preferably a group of formula —CH$_2$CH$_2$CN, —CH$_2$CH$_2$—Si(CH$_3$)$_2$C$_6$H$_5$, —CH$_2$CH$_2$—S(O)$_2$—CH$_2$CH$_3$, —CH$_2$CH$_2$—C$_6$H$_4$—NO$_2$, —CH$_2$CH$_2$—Si(CH$_3$)$_2$C$_6$H$_5$, —CH$_2$CH$_2$—S(O)$_2$—CH$_2$CH$_3$, or —CH$_2$CH$_2$—C$_6$H$_4$—NO$_2$. $R^4$ represents a substituted or unsubstituted aliphatic group, especially a $C_{1-6}$ aliphatic group (e.g., methyl, ethyl, methoxyethyl or allyl); a substituted or unsubstituted aryl, such as a phenyl, group; a substituted or unsubstituted aralkyl, such as a benzyl, group; an alcohol protecting group, especially a base-labile or a silyl protecting group, such as a tri(alkyl)silyl, especially tri($C_{1-4}$ alkyl)silyl, preferably a trimethylsilyl group or a t-butyldimethylsilyl group; or —(CH$_2$)$_q$—NR$^9$R$^{10}$. $R^5$ and $R^6$ are each, independently a substituted or unsubstituted aliphatic group, especially a $C_{1-6}$ aliphatic group, preferably a $C_{1-4}$ alkyl group, or an amine protecting group. Alternatively, $R^5$ and $R^6$ taken together with the nitrogen to which they are attached form a heterocyclyl group, preferably comprising a 5 or 6-membered ring. $R^7$ represents a substituted or unsubstituted aliphatic group, especially a $C_{1-6}$ aliphatic group preferably a $C_{1-4}$ alkyl group, or a thiol protecting group. $R^9$ and $R^{10}$ are each, independently, —H, a substituted or unsubstituted aryl group, such as a phenyl group, a substituted or unsubstituted aliphatic group, especially a $C_{1-6}$ aliphatic group preferably a $C_{1-4}$ alkyl group, a substituted or unsubstituted aralkyl group, such as a benzyl group, or an amine protecting group. Alternatively, $R^9$ and $R^{10}$ taken together with the nitrogen to which they are attached form a heterocyclyl group, preferably comprising a 5 or 6-membered ring. q is an integer from 1 to about 6. Each $R^3$ independently is a $C_{1-6}$ alkyl group, preferably an isopropyl group. Substituents which may be present are selected so as not to interfere with oligonucleotide synthesis, and include alkyl, especially $C_{1-4}$ alkyl groups; halo, especially chloro and fluoro groups; aryl groups, especially phenyl groups; cyano groups; alkoxy, especially $C_{1-4}$alkoxy, groups; protected hydroxyl groups; protected amino groups; and blocked amino groups, such as di$C_{1-4}$alkylamino groups. The phosphoramidite employed is commonly a betacyanoethyl-N,N-diisopropyl phosphoramidite.

Nucleoside bases include naturally occurring bases, such as adenine, guanine, cytosine, thymine, and uracil and modified bases such as 7-deazaguanine, 7-deaza-8-azaguanine, isoguanine, isocytosine, 5-propynylcytosine, 5-propynyluracil, 7-deazaadenine, 7-deaza-8-azaadenine, 7-deaza-6-oxopurine, 6-oxopurine, 3-deazaadenosine, 2-oxo-5-methylpyrimidine, 2-oxo-4-methylthio-5-methylpyrimidine, 2-thiocarbonyl-4-oxo-5-methylpyrimidine, 4-oxo-5-methylpyrimidine, 2-amino-purine, 5-fluorouracil, 2,6-diaminopurine, 8-aminopurine, 4-triazolo-5-methylthymine, 4-triazolo-5-methyluracil and hypoxanthine.

The nucleoside base may be protected. Examples of suitable protecting groups are well known in the art. Typically, nucleoside bases have amine groups which can be protected with an amine protecting group, such as an amide or a carbamate. For example, the amine groups of adenine and cytosine are typically protected with benzoyl protecting groups, and the amine groups of guanine is typically protected with an isobutyryl group, a 4-isopropylphenoxyacetyl group or t-butylphenoxyacetyl group. However, other protection schemes, such as formamidine, may be used. For example, for fast deprotection, the primary amine groups of adenine and guanine are protected with phenoxyacetyl groups and the amine group of cytosine is protected with an isobutyryl group or an acetyl group.

It will be recognised that, whilst the Formula (1) is expressed in terms of the natural, nucleosidic configuration (D-isomers), the present invention is equally applicable to the corresponding synthetic or unnatural configuration (L-isomers), to alpha and beta anomeric forms, and to mixtures of configurations.

H-phosphonates which may be employed in the process of the present invention are preferably nucleoside H-phosphonate monoesters, especially those having the general chemical formula (2):

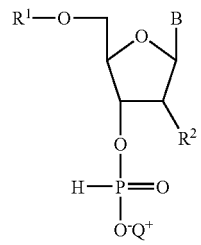

wherein $R^1$, $R^2$ and B are as described above for formula (1), and Q represents an ammonium cation, such as a primary, secondary or tertiary $C_{1-4}$alkyl ammonium ion, and especially a triethylammonium ion.

Oligonucleotides that can be prepared by the process of the present invention include oligodeoxyribonucleotides, oligoribonucleotides, and oligonucleotides comprising mixtures of deoxyribo- and ribonucleotides. The oligonucleotides may be modified by one or more modifications known in the field of oligonucleotide chemistry, for example ribonucleotide moieties may be modified at one or more of the 2'-positions by the presence of 2'-alkoxy group, such as a methoxy or methoxyethoxy group. Deoxyribonucleotide moieties may be modified at the 2'-position by the presence of a substituent, such as a halo group, especially a fluoro group, or by an alkenyl group such as an allyl group. Abasic nucleotide moieties may also be present. One or more locked nucleotides may be present. In many embodiments, the oligonucleotides will be in the form of the natural D-isomer. However, some or all of the oligonucleotide may represent an unnatural isomer, for example an L-isomer or an alpha-anomer, either in whole or in part. The internucleoside linkages may be natural phosphate, or one or more modified linkages, for example phosphorothioate, phosphorodithioate or phosphoramidate linkages may be present.

The oligonucleotides may comprise natural and/or unnatural nucleobases including adenine, guanine, cytosine, thymine, uracil, 7-deazaguanine, 7-deaza-8-azaguanine, isoguanine, isocytosine, 5-propynylcytosine, 5-propynyluracil, 7-deazaadenine, 7-deaza-8-azaadenine, 7-deaza-6-oxopurine, 6-oxopurine, 3-deazaadenosine, 2-oxo-5-methylpyrimidine, 2-oxo-4-methylthio-5-methylpyrimidine, 2-thiocarbonyl-4-oxo-5-methylpyrimidine, 4-oxo-5-methylpyrimidine, 2-amino-purine, 5-fluorouracil, 2,6-diaminopurine, 8-aminopurine, 4-triazolo-5-methylthymine, 4-triazolo-5-methyluracil and hypoxanthine.

Oligonucleotides produced by the process of the present invention commonly comprise from 8 to 100 nucleobases and preferably from about 12 to about 40 nucleobases, such as from about 16 to 30 nucleobases.

Oligonucleotides produced by the process of the present invention often comprise 20% or more phosphate internucleotide linkages, the remainder being modified linkages, especially phosphorothioate linkages. Preferably the oligonucleotides comprise 50% or more, especially 75% or more, and, most preferably, 100% phosphate internucleotide linkages.

Most commonly, the oligonucleotides produced are oligodeoxyribonucleotides.

When the oligonucleotide is prepared using the phosphoramidite approach, the coupling of the oligonucleotide synthon is most commonly carried out in the presence of an activator. Activators which can be employed in the process of the present invention include tetrazole and substituted tetrazoles, such as S-ethylthiotetrazole and S-benzylthiotetrazole; substituted imidazoles, such as 2- or 4-alkylthioimidazoles, 2- or 4-nitroimidazole, 2- or 4-haloimidazoles, or cyanoimidazoles, particularly 2,4-dicyanoimidazole; salts of heteroaromatic compounds comprising fewer than four nitrogen atoms in the heteroaromatic ring, especially heteroaromatic compounds comprising a 5 or 6 membered ring which comprises one or two nitrogen atoms. Examples include pyridinium, imidazolinium and benzimidazolinium salts, particularly the hexafluorophosphate, tetrafluoroborate, triflate, hydrochloride, trifluoroacetate, dichloroacetate, O-mesyl, O-tosyl, bromide or trifluorosulphonyl salts as disclosed in PCT application WO 99/62922 (incorporated herein by reference); benzotriazole and derivatives thereof, especially hydroxybenzotriazole; and saccharin or a saccharin derivative as disclosed in PCT application WO03/004512 (incorporated herein by reference), preferably employed as a salt-complex formed with an organic base, especially the N-methylimidazole, pyridine or 3-methylpyridine salts of saccharin.

The oligonucleotide may comprise one or more protecting groups. Examples of such protecting groups, and the positions which they can be employed to protect, are well known to those skilled in the art, and include trityl, monomethoxytrityl and dimethoxytrityl groups, levulinoyl groups, isobutyryl groups, benzoyl groups, acetyl groups and carbonate groups, such as BOC and especially FMOC. It is especially preferred that the coupling site on the nascent oligonucleotide which reacts with the oligonucleotide synthon, commonly a thiol or, particularly, a hydroxyl group, is protected with an acid labile protecting group, most especially a trityl, monomethoxytrityl or dimethoxytrityl group.

The coupling site on the nascent oligonucleotide is preferably located at the 5'-position of a ribose or deoxyribose moiety.

The process according to the present invention can be carried out as a solution phase process, but is preferably carried out as a solid phase process. Solid-phase process for the synthesis of oligonucleotides are well known in the art. The nascent oligonucleotide, which may at the commencement of the process comprise a single nucleoside residue, is attached to the solid support, and the step-wise assembly process carried out. The oligonucleotide synthesis can take place by direct attachment to a functional group of the solid support. However, in many embodiments, it is preferred to employ a cleavable linker to attach the oligonucleotide to the solid support. Examples of such linker are well known in the art and include particularly succinyl, oxaloyl and trityl linkers.

The oligonucleotide can be attached to the solid support at any convenient position, including attachment via a nucleobase. However, in many embodiments, the oligonucleotide comprises a ribose or deoxyribose ring attached to the solid support via either the 5'-position or, preferably, the 3'-position.

Solid supports which can be employed in the process of the present invention are well known in the art, and include silica, controlled pore glass, polystyrene, copolymers comprising polystyrene such as polystyrene-poly(ethylene glycol) copolymers and polymers such as polyvinylacetate. Additionally, poly(acrylamide) supports, especially microporous or soft gel supports, such as those more commonly employed for the solid phase synthesis of peptides may be employed if desired. Preferred poly(acrylamide) supports are amine-functionalised supports, especially those derived from supports prepared by copolymerisation of acryloyl-sarcosine methyl ester, N,N-dimethylacrylamide and bis-acryloylethylenediamine, such as the commercially available (Polymer Laboratories) support sold under the catalogue name PL-DMA. The procedure for preparation of the supports has been described by Atherton, E.; Sheppard, R. C.; in *Solid Phase Synthesis: A Practical Approach*, Publ., IRL Press at Oxford University Press (1984). The functional group on such supports is a methyl ester and this is initially converted to a primary amine functionality by reaction with an alkyl diamine, such as ethylene diamine.

The process according to the present invention may employ such process steps as are conventionally carried out for the solid-phase synthesis of oligonucleotides using phosphoramidite chemistry, including sulfurization and capping stages.

When a sulphurization agent is employed, the sulphurization agent may comprise elemental sulfur. Preferably, the sulfurization agent is an organic sulfurization agent.

Examples of organic sulfurization agents include 3H-benzodithiol-3-one 1,1-dioxide (also called "Beaucage reagent"), dibenzoyl tetrasulfide, phenylacetyl disulfide, N,N,N',N'-tetraethylthiuram disulfide, and 3-amino-[1,2,4]-dithiazole-5-thione (see U.S. Pat. No. 6,096,881, the entire teachings of which are incorporated herein by reference).

Typical reaction conditions for sulfurization of an oligonucleotide using the above agents can be found in Beaucage, et al., *Tetrahedron* (1993), 49:6123, which is incorporated herein by reference.

Preferred sulfurization reagents are 3-amino-[1,2,4]-dithiazole-5-thione and phenylacetyl disulfide.

Sulfurization of an oligonucleotide may be carried out by, for example use of a solution of 3-amino-[1,2,4]-dithiazole-5-thione in an organic solvent, such pyridine/acetonitrile (1:9) mixture or pyridine, having a concentration of about 0.05 M to about 0.2 M.

After oxidation or sulfurization of the oligonucleotide, any unreacted free hydroxy or thiol groups can be capped so that they cannot react in subsequent coupling steps. Capping failure sequences allows them to be more readily separated from full length oligonucleotide product. Any reagent which will react with a hydroxy or thiol group and prevent it from reacting with an oligonucleotide synthon can be used as a capping reagent. Typically, an anhydride, such as acetic anhydride or isobutyric anhydride, or an acid chloride, such as acetyl chloride or isobutyryl chloride, in the presence of a base is used as a capping reagent.

Acid labile protecting groups which protect the coupling site on the nascent oligonucleotide are commonly removed with a solutions of dichloroacetic acid. Dichloroacetic acid solutions which can be employed are commonly solutions comprising dichloromethane or, preferably, a hydrocarbon solvent, most preferably toluene. In many embodiments, solutions comprising up to about 10% v/v of dichloroacetic acid are employed, and preferably from about 1 to 5%, such as about 3% v/v.

When the oligonucleotide is assembled by solid phase synthesis, on completion of the assembly of the desired product, the product may be cleaved from the solid support, preferably following either total deprotection of the product, whereby all protecting groups are removed, or partial deprotection whereby protecting groups other than the protecting group on the terminal coupling site, commonly an acid labile protecting group protected 5'-hydroxyl, are removed. Cleavage methods employed are those known in the art for the given solid support. When the product is bound to the solid support via a cleavable linker, cleavage methods appropriate for the linker are employed, for example contact with methylamine, aqueous methylamine solution, gaseous ammonia and particularly contact with concentrated aqueous ammonia solution. Following cleavage, the product can be purified using techniques known in the art, such as one or more of ion-exchange chromatography, reverse phase chromatography, and precipitation from an appropriate solvent. Further processing of the product by for example ultrafiltration may also be employed.

Where the oligonucleotide is purified, or partially purified, with the terminal coupling site protecting group in place, the protecting group may be removed by contact by methods known in the art. For example, an acid-labile protecting group can be removed with an acidic solution, such as acetic acid solution. Further purification may then be carried out.

In particularly preferred embodiments, the process of the present invention employs betacyanoethyloxy nucleoside phosphoramidites as oligonucleotides, and the oxidation step employed comprises oxidation with aqueous iodine in the presence of a base the conjugate acid of which has a pKa in the range of from 6.5 to 7.5.

The present invention is illustrated without limitation by the following examples.

COMPARATIVE EXAMPLE 1

A 26-mer phosphate diester oligonucleotide was synthesised using conventional phosphoramidite chemistry on an AKTA Oligo Pilot using PS200 as solid supports and saccharin-N methylimidazole salt complex (prepared as described in International patent application WO03/004512) as an activator. Two molar equivalents of betacyanoethyloxy phosphoramidites were used and the ratio of number of equivalents of phosphoramidite to activator was 1:1. The synthesis was carried out at 3 mmol scale.

The standard synthesis steps as described below were used:
(i) Detritylation with 3% v/v dichloroacetic acid in toluene;
(ii) wash with acetonitrile;
(iii) coupling;
(iv) wash with acetonitrile;
(v) oxidation with 50 mM iodine in pyridine:water (9:1 v/v);
(vi) wash with acetonitrile;
(vii) cap using Cap A solution (20% v/v N-methylimidazole, 30% v/v pyridine in acetonitrile) and Cap B solution (20% v/v isobutyric anhydride in acetonitrile) and repeat steps (i) to (vii) to complete the synthesis, the capping step being omitted after the final coupling step.

On completion of the synthesis, the oligonucleotide was cleaved and deprotected using 20% v/v t-butylamine in acetonitrile to remove cyanoethyl groups, followed by treatment with concentrated aqueous ammonia solution.

A 55% yield of full length product was obtained.

EXAMPLE 2

The synthesis of Example 1 was repeated, except that, prior to oxidation but after wash step iv), 0.5 column volumes of Cap A solution was passed into the column.

A 62% yield of full length product was obtained.

EXAMPLE 3

The synthesis of Example 2 was repeated, except that a CPG support was employed.

A 73% yield of full length product was obtained.

EXAMPLE 4

The synthesis of Example 1 was repeated, except at 1 mmol scale, and employing as oxidant a 50 mM solution of iodine in pyridine:N-methylimidazole:water (7:2:1 by volume).

A 62% yield of full length product was obtained.

COMPARATIVE EXAMPLE 5

A second 26-mer phosphate diester oligonucleotide was synthesised using conventional phosphoramidite chemistry on an AKTA Oligo Pilot using PS200 as solid supports and saccharin-N methylimidazole salt complex (prepared as described in International patent application WO03/004512) as an activator. Two molar equivalents of betacyanoethyloxy phosphoramidites were used and the ratio of number of equivalents of phosphoramidite to activator was 1:1. The synthesis was carried out at 1 mmol scale.

The standard synthesis steps as described below were used:
(i) Detritylation with 3% v/v dichloroacetic acid in toluene;
(ii) wash with acetonitrile;
(iii) coupling;

(iv) wash with acetonitrile;
(v) oxidation with 50 mM iodine in pyridine:water (9:1 v/v);
(vi) wash with acetonitrile;
(vii) cap using Cap A solution (20% v/v N-methylimidazole, 30% v/v pyridine in acetonitrile) and Cap B solution (20% v/v isobutyric anhydride in acetonitrile) and repeat steps (i) to (vii) to complete the synthesis, the capping step being omitted after the final coupling step.

On completion of the synthesis, the oligonucleotide was cleaved and deprotected using 20% v/v t-butylamine in acetonitrile to remove cyanoethyl groups, followed by treatment with concentrated aqueous ammonia solution.

A 50% yield of full length product was obtained.

EXAMPLE 6

The synthesis of Example 5 was repeated, except that, prior to oxidation but after wash step iv), 0.5 column volumes of Cap A solution was passed into the column.

A 57% yield of full length product was obtained.

EXAMPLE 7

The synthesis of Example 5 was repeated, except that a CPG support was employed.

A 70% yield of full length product was obtained.

COMPARATIVE EXAMPLE 8

The 26-mer phosphate diester oligonucleotide prepared in Example 5 was synthesised using conventional phosphoramidite chemistry on an AKTA Oligo Pilot using controlled pore glass as solid support and dicyanoimidazole (0.7M in acetonitrile) as an activator. Two molar equivalents of betacyanoethyloxy phosphoramidites were used and the ratio of number of equivalents of phosphoramidite to activator was 1:3.5. The synthesis was carried out at 3 mmol scale.

The standard synthesis steps as described below were used:
(i) Detritylation with 3% v/v dichloroacetic acid in toluene;
(ii) wash with acetonitrile;
(iii) coupling;
(iv) wash with acetonitrile;
(v) oxidation with 50 mM iodine in pyridine:water (9:1 v/v);
(vi) wash with acetonitrile;
(vii) cap using Cap A solution (20% v/v N-methylimidazole, 30% v/v pyridine in acetonitrile) and Cap B solution (20% v/v isobutyric anhydride in acetonitrile) and repeat steps (i) to (vii) to complete the synthesis, the capping step being omitted after the final coupling step.

On completion of the synthesis, the oligonucleotide was cleaved and deprotected using 20% v/v t-butylamine in acetonitrile to remove cyanoethyl groups, followed by treatment with concentrated aqueous ammonia solution.

A 56% yield of full length product was obtained.

EXAMPLE 9

The synthesis of Example 8 was repeated, except that, prior to oxidation but after wash step iv), 0.5 column volumes of Cap A solution was passed into the column.

A 62% yield of full length product was obtained.

The invention claimed is:

1. A process for the preparation of an oligonucleotide having at least one phosphate internucleotide linkage comprising the steps of:
    a) forming a nascent oligonucleotide comprising a phosphorus (III) internucleotide linkage; and
    b) oxidation of the nascent oligonucleotide with aqueous iodine solution thereby to form a phosphorus (V) internucleotide linkage; wherein the oligonucleotide is prepared using solid phase chemistry, and the oligonucleotide is washed with a washing solution comprising the base immediately before oxidation;
    wherein the oxidation is carried out in the presence of a base, the conjugate acid of said base having a pKa higher than the pKa of the conjugate acid of pyridine.

2. A process according to claim 1, wherein the phosphorus (III) internucleotide linkage is formed by coupling a nucleoside phosphoramidite to a free hydroxyl or thiol group attached to a nascent oligonucleotide.

3. A process according to claim 2, wherein the nucleoside phosphoramidite is a nucleoside 3'-(betacyanoethyl) phosphoramidite.

4. A process according to claim 1, wherein the pKa of the conjugate acid of the base employed is 5.4 or greater and less than 12.

5. A process according to claim 4, wherein the pKa of the conjugate acid of the base employed is from 6.5 to 7.5.

6. A process according to claim 1, wherein the washing solution comprises up to 50% v/v base.

7. A process according to claim 1, wherein the washing solution comprises 20% v/v N-methylimidazole and 30% v/v pyridine in acetonitrile.

8. A process according to claim 1, wherein the base is N-methylimidazole.

9. A process according to claim 1, wherein the oligonucleotide which is oxidised comprises an acid labile protecting group.

10. A process according to claim 9, wherein the acid labile protecting group is located at the 5'-position of an oligoribonucleotide or an oligodeoxyribonucleotide.

11. A process according to claim 9 or 10, wherein the acid labile protecting group is a dimethoxytrityl group.

12. A process according to claim 1, wherein the oligonucleotide prepared comprises 20% or more phosphate internucleotide linkages.

13. A process according to claim 12, wherein the oligonucleotide comprises 50% or more phosphate internucleotide linkages.

14. A process according to claim 12, wherein the oligonucleotide comprises 100% phosphate internucleotide linkages.

15. A process according to claim 6, wherein the washing solution comprises from 10-30% v/v base.

* * * * *